United States Patent [19]

Wilson et al.

[11] Patent Number: 5,591,429
[45] Date of Patent: Jan. 7, 1997

[54] **COMPOSITION CONTAINING 2-DEOXY-D-GLUCOSE AND *CANDIDA SAITOANA* AND A METHOD OF USE FOR THE BIOLOGICAL CONTROL OF POSTHARVEST DISEASES**

[75] Inventors: Charles L. Wilson; Ahmed E. Ghaouth, both of Frederick, Md.

[73] Assignee: The United States of America as represented by the Secretary of Agriculture, Washington, D.C.

[21] Appl. No.: 95,552

[22] Filed: Jul. 26, 1993

[51] Int. Cl.$^6$ ............................. A01N 63/00; C12N 1/16
[52] U.S. Cl. ..................................... 424/93.51; 435/255.2
[58] Field of Search ..................................... 424/93, 93 D, 424/93.51, 255.2; 435/252.2

[56] References Cited

U.S. PATENT DOCUMENTS

| | | | |
|---|---|---|---|
| 4,764,371 | 8/1988 | Pusey | 424/93 |
| 5,041,384 | 8/1991 | Wilson et al. | 435/255 |
| 5,047,239 | 9/1991 | Pusey | 424/93 |

OTHER PUBLICATIONS

Zonneveld, B., *Developmental Biology*, vol. 34, pp. 1–8 (1973).
Biely et al., *J. of Bacteriology*, vol. 107 (1) pp. 121–129 (1971).
Johnson, B., *J. of Bacteriology*, vol. 95 (1), pp. 1169–1172 (1968).
Atkins et al., *Ann. App. Biol.*, vol. 53, pp. 437–443 (1964).
Barnett et al., *Science*, vol. 114, pp. 439–444 (1951).
Wilson et al., *Ann. Rev. Phytopathol.*, vol. 27, pp. 425–441 (1989).
Wilson et al., *Scientia Horticulturae*, vol. 53, pp. 183–189 (1993).
McLaughlin et al., *Phytopathology*, vol. 80 (5) pp. 456–461 (1990).
Nakase et al, *J. Gen. Appl. Microbiol.*, 31:71–86 (1985).
Suresh et al, *J. Appl. Bacter.*, 52:1–4 (1982).
Lodder, *The Yeasts*: A Taxonomic Study, Amsterdam: North-Holland Publishing Co., (1952), pp. 414–417.

*Primary Examiner*—Irene Marx
*Attorney, Agent, or Firm*—M. Howard Silverstein; John Fado; Janelle S. Graeter

[57] ABSTRACT

A biocontrol composition comprising an antagonistic microorganism and a sugar analog (2-deoxy-D-glucose) gives a level of control superior to that of either component when used alone and comparable to that of synthetic chemical fungicides. The antagonistic microorganism is an isolate of *Candida saitoana* and has resistance to the fungicidal activity of sugars and sugar analogs.

9 Claims, 2 Drawing Sheets

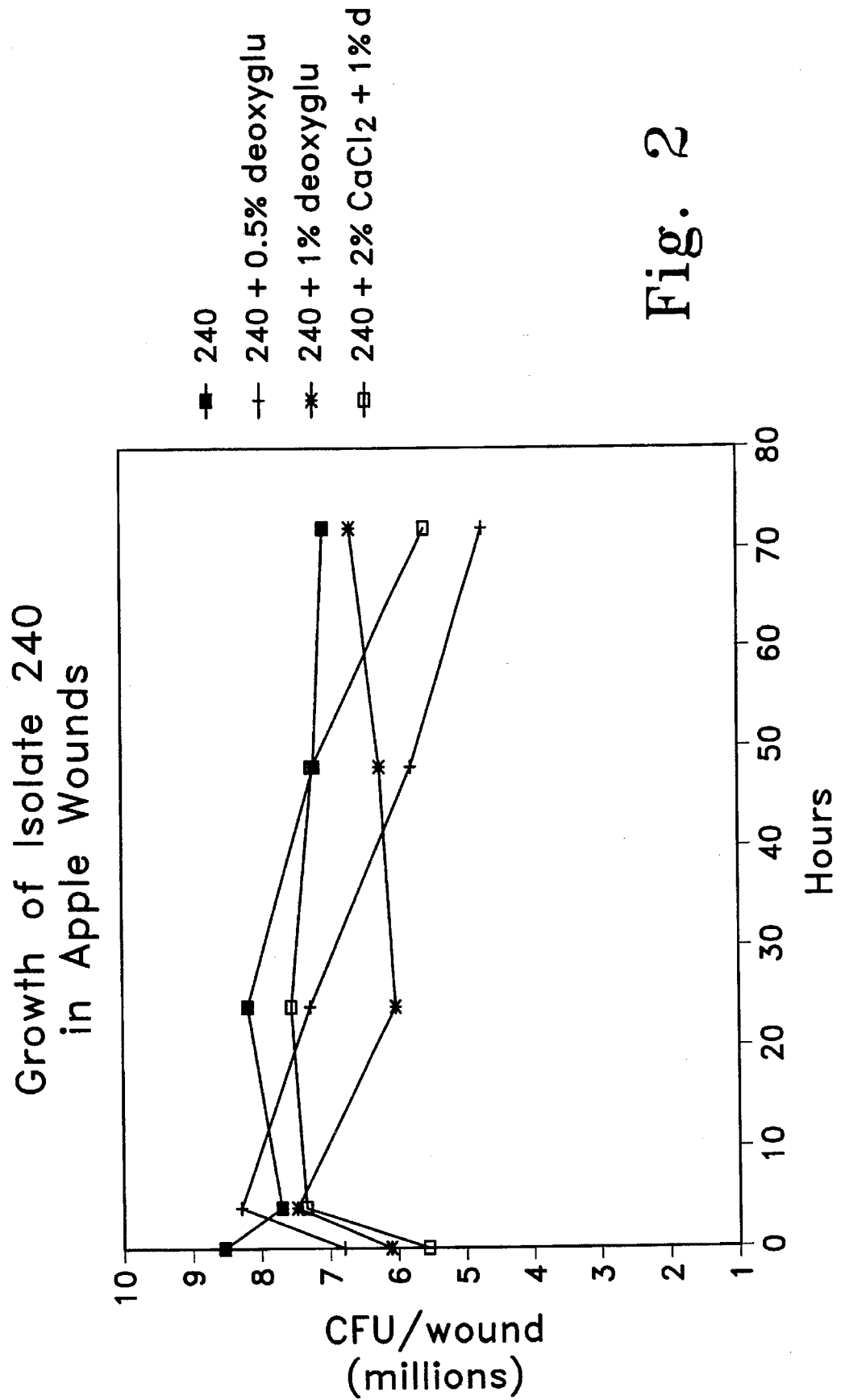

COMPOSITION CONTAINING 2-DEOXY-D-GLUCOSE AND *CANDIDA SAITOANA* AND A METHOD OF USE FOR THE BIOLOGICAL CONTROL OF POSTHARVEST DISEASES

BACKGROUND OF THE INVENTION

1. Field of the Invention

It is estimated that approximately 25% of our harvested fruits and vegetables are lost to postharvest diseases. In the past, synthetic chemical fungicides were relied upon for the control of such diseases; however, as concerns over the health risks posed by these chemicals have increased, many of them have been withdrawn from use by regulatory agencies as well as a result of consumer pressure. In addition, an increased resistance to fungicide treatment by the pathogens responsible for postharvest diseases has been observed. Thus, there is a strong incentive to develop safe and effective alternatives to chemical fungicides. This invention relates to a composition which provides such an alternative by utilizing an antagonistic microorganism (*Candida saitoana*) in combination with the sugar analog, 2-deoxy-D-glucose (2-DG).

2. Description of the Prior Art

The biological control of postharvest diseases by antagonistic microorganisms has become increasingly important with the advent of tighter controls on the use of chemical additives on agricultural food commodities. As a result, a number of investigators have applied compositions containing such microorganisms to agricultural commodities with some success.

The bacterium *Bacillus subtilis* has been shown to inhibit a variety of diseases such as brown rot (*Monilinia fructicola*) on peaches and other stone fruit and brown rot, gray mold rot (*Botrytis cinerea*) and bitter rot (*Glomerella cingulata*) on apples (Pusey et al, U.S. Pat. No. 4,764,371, 1988, and Pusey, U.S. Pat. No. 5,047,239, 1991). *Pichia guilliermondii* (anamorph *Candida guilliermondii*) was shown to be effective against a number of pathogens including *Botrytis cinerea*, *Pencillium expansum* and *Alternaria alternata* (Wilson et al., U.S. Pat. No. 5,041,384, 1991). McLaughlin et al. (*Phytopathology*, 1990) and Wilson et al. (*Scientia Horticulturae*, 1993) also have shown that various strains of Candida sp. were effective against *Botrytis cinerea* and *Pencillium expansum* in apples. A review of biocontrol technology was presented by Wilson and Wisniewski (*Ann. Rev. Phytopathol.*, 1989). In addition to the use of microorganisms, the use of sugars and sugar analogs has also recently been investigated for application as fungicides on agricultural commodities (El -Ghaouth and Wilson, unpublished results). The antifungal property of sugar analogs is well documented; however, few attempts had been made to utilize them as fungicides (Barnett and Lilly, *Science*, 1951; Atkin et al., *Ann Appl. Biol.*, 1964). The antifungal activity of 2-DG in particular has long been known (Johnson, *J. Bacteriology*, 1968; Biely et al., *J. Bacteriology*, 1971; Zonneveld, *Developmental Biology*, 1973); however, exploitation of this property for the inhibition of postharvest diseases on fruits and vegetables was not attempted.

Although biological control agents have proved safe and effective, the antagonistic effect has often fallen short of that achieved by chemical fungicides. A search for improvements has therefore continued in order to obtain biological control equal to, if not better than, that obtainable by chemical means.

SUMMARY OF THE INVENTION

We have discovered a novel biocontrol composition comprising a strain of the antagonistic microorganism *Candida saitoana* (*C. saitoana*) and the sugar analog 2-deoxy-D-glucose (2-DG). The combination gives control superior to that of antagonist alone and comparable to that achieved with synthetic chemical fungicides.

Accordingly, it is an object of the invention to provide a novel biocontrol composition which is an effective inhibitor of postharvest diseases in fruits and vegetables.

It is also an object of the invention to provide a method of treating fruits and vegetables for the control of postharvest diseases by the application of effective amounts of the novel composition.

Other objects and advantages will become readily apparent from the following description.

BRIEF DESCRIPTION OF THE DRAWINGS

FIG. 2 shows the growth of *C. saitoana* isolate 240 in apple wounds alone and in the presence of 0.5% 2-DG, 1% 2-DG and the combination of 2% $CaCl_2$ and 1% 2-DG.

Figure 1:
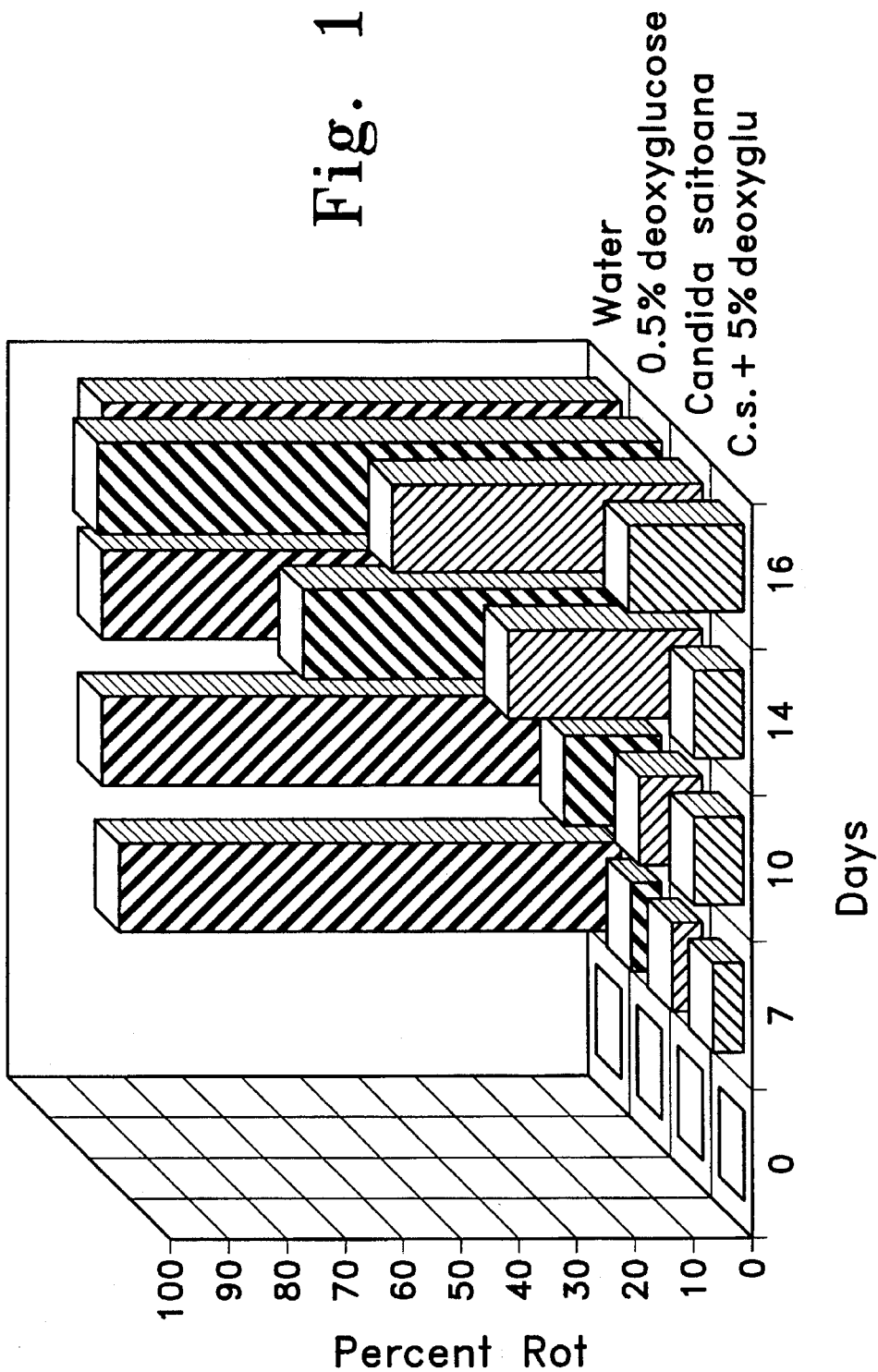
FIG. 1 shows the percent rot of apples treated with 0.5% 2-DG, *C. saitoana* and the combination of *C. saitoana* and 0.5% 2-DG. Water served as the control.

All percents are given in wt/vol.

DETAILED DESCRIPTION OF THE INVENTION

Since 2-DG showed effectiveness as an antifungal agent in the control of postharvest diseases (El -Ghaouth and Wilson, supra), the possibility existed that it would be a useful additive to biocontrol compositions utilizing antagonistic microorganism, provided that an effective microorganism which was also resistant to the fungicidal activity of the sugar analog could be found. Isolate 240 of *C. saitoana* was found to meet those requirements. Although some Candida species were known to be antagonists to postharvest diseases (McLaughlin et al., 1990, Wilson et al., 1993 and Wilson and Wisniewski, 1989, supra), such activity by *C. saitoana* was previously unknown.

*C. saitoana* isolate 240 was obtained from the surface of citrus fruit by repeatedly washing the fruit with sterile water. The microorganism was thereafter plated and grown on any nutritionally rich medium sufficient to support the growth of microorganisms. Preferably, the medium was either yeast dextrose agar (NYDA) or yeast malt extract agar (YM).

The isolate was identified as *Candida saitoana* Nakase & Suzuki based on morphological and physiological characteristics at the German Collection of Microorganisms and Cell cultures, Braunschweig, Germany, and the Centraalbureau voor Schimmelcultures, Delft, the Netherlands.

The isolate had the following morphological characteristics: colonies on malt extract agar were smooth and butyrous with lobate margins; blastospores were 4–7µ and were globose ellipsoidal; no mycelium and pseudomycelium were present; and no sexual reproduction was detected.

Utilization of carbon and nitrogen sources was tested, and the results are shown in Table 1. In addition, no growth was observed at 37° C. or in the presence of 60% glucose.

TABLE 1

Utilization of C- and N-sources

| Anaerobic: | | | |
|---|---|---|---|
| Glucose | − | | |
| Aerobic: | | | |
| Glucose | + | α-methylglycoside | + |
| Galactose | + | Salicin | + |
| Sorbose | + | Cellobiose | + |
| Rhamnose | − | Maltose | + |
| Dulcit | − | Lactose | + |
| Inositol | − | Melibiose | + |
| Mannitol | + | Sucrose | + |
| Sorbitol | + | Trehalose | + |
| Glycerol | + | Inulin | + |
| Erythritol | − | Melezitose | − |
| D-Arabinose | − | Raffinose | + |
| L-Arabinose | w | Starch | − |
| Ribose | − | Xylitol | + |
| D-Xylose | + | Gluconate | − |
| L-Xylose | − | 2-keto-Gluconate | + |
| Adonitol | + | 5-keto-Gluconate | − |
| | | 1,2 propanediol | + |
| | | Nitrate | − |
| | | Ethylamine | − | w = weak

Conventional screening procedures were carried out to test the ability of the isolate to grow in the presence of 2-DG. Culture conditions known to be effective for Candida sp. were utilized, with the exception that 2-DG in concentrations in the range of 0.01% to 0.1% was added to the growth medium.

Cultures may be grown under aerobic conditions at any temperature which is effective, i.e. from about 10° C. to about 30° C. The preferred range is from about 20° C. to about 25° C. The pH of the growth medium is about neutral, i.e. pH 6.7 to 7.2. Incubation time is the amount of time required for the microorganisms to reach a stationary growth phase, preferably from about 40 to about 60 hours.

The isolate may be grown in any conventional shake flask for small fermentation runs. Large scale operations, however, may be carried out in a fermentation tank, while applying agitation and aeration to the inoculated liquid medium. Following incubation, microorganisms are harvested by conventional sedimentation means, such as centrifugation or filtering. Cultures may be stored on silica gel and frozen until needed for use.

Samples of the isolate were deposited with the culture collection at the Northern Regional Research Center, U.S. Department of Agriculture, Peoria, Ill. 61604, under the acquisition number NRRL Y-21022 on Dec. 3, 1992. The deposited material was accepted for deposit under the Budapest Treaty on the International Recognition of the Deposit of Microorganisms for the purpose of patent procedures. Further, the depository affords permanence of the deposits and ready accessibility thereto by the public if a patent is granted, and the material has been deposited under conditions that assure that access to the material will be available during the pendency of the patent application to one determined by the Commissioner of Patents and Trademarks to be entitled thereto under 37 CFR 1.14 and 35 USC 122. All restrictions on the availability of the deposited material to the public will be irrevocably removed upon the granting of the patent.

Solutions of 2-DG (Sigma Chemical Co., St. Louis, Mo.) were prepared by dissolving a sufficient amount of the sugar analog in sterile deionized water and membrane filtering.

The novel composition was prepared by adding a sufficient amount of the 2-DG solution to a suspension containing an effective amount of microorganisms. An effective amount is that concentration which inhibits the growth and development of the targeted pathogen when applied to the fruit. An effective concentration may vary, depending on such factors as (1) the type of fruit, (2) the ripeness of the fruit, (3) the estimated concentration and type of pathogens, (4) the type of wound on the fruit and (5) the temperature and humidity. Exemplary concentrations range from about $10^7$ to about $10^9$ CFU/ml, preferably about $10^7$ to about $10^8$ CFU/ml. Effective amounts of 2-DG range from about 0.01% (w/v) to about 1.0% (w/v), preferably about 0.05% (w/v) to about 0.1% (w/v).

The composition is preferably applied as a suspension in water, however, the liquid medium in which the microorganism is grown is also suitable. In addition, conventional additives such as surfactants and wetting agents may also be included in the composition in order to enhance its effectiveness.

The composition is useful for the control of postharvest diseases in a variety of fruit including, but not limited to, apples & peaches.

The composition may be applied to fruits utilizing conventional application methods such as dipping, spraying or brushing. In addition, it may also be incorporated into waxes, wraps or other protective coatings used in processing the fruits. Applications may be made at any time before or after harvest, however, treatment preferably occurs after harvest and prior to storage or shipment.

The following example is intended to further illustrate the invention and not to limit the scope of the invention as defined by the claims.

EXAMPLE

The effect of different treatments (0.5% 2-DG, 10 CFU/ml C. saitoana and 0.5% 2-DG+C. saitoana) on the decay of apples inoculated with Botrytris cinerea (B. cinerea) was investigated. Apples were wounded (3 mm×5 mm), and 50 μl of each treatment was placed in each wound (control apple wounds received water). The wounds were allowed to dry 30 min at room temperature. After air drying, the wounds were challenged with 30 μl of a spore suspension of B. cinerea consisting of $10^5$ conidia/ml. There were four replicates of 50 fruit per treatment with complete randomization. Lesion diameter and percent infection were determined for each treatment at 7, 10, 14 and 16 days after challenge. The tests were repeated four times, and the data were analyzed by analysis of variance. In order to determine the survival of the yeast in the presence of 2-DG at the wound site, scrapings were made of the wound surface at various times. These scrapings were diluted serially in sterile water, plated on potato dextrose agar, and the yeast growth observed.

The study demonstrated that the combination of 2-DG and C. saitoana was more effective in controlling B. cinerea rot of apple than either 2-DG or C. saitoana alone (FIG. 1). After 16 days of storage at 24° C., less than 20% of the apples treated with the combination of 2-DG and C. saitoana developed infection, while in fruit treated with either 2-DG or C. saitoana alone, more than 95% and 55%, respectively, of the fruit were diseased. A synergistic effect exhibited by the combination of the two components of the composition is therefore strongly suggested.

The inhibitory effect of this combination is further amplified at low temperatures. A complete control of decay was achieved for up to 35 days of storage at 4° C.

The effectiveness of the combination of 2-DG and *C. saitoana* in controlling decay appears to stem from the interplay of the biological activity of *C. saitoana* and the antifungal property of 2-DG. Sugar analogs, such as L-sorbose and 2-DG, are known to interfere with the growth of several yeasts and some filamentous fungi when used as a sole carbon source (Atkin et al., 1964; Biely et al., 1971; *supra*). Their ability to readily form phosphate esters that cannot be further metabolized and that interfere with the metabolic processes implicated in cell wall biosynthesis is believed to be the basis of their antifungal action in yeasts. In the case of 2-DG, its inhibitory activity has been extensively studied in yeasts where it was found to affect cell wall-forming enzymes, namely β-1,3-glucan synthetase (Biely et al., 1971, *supra*). Very little information is known, however, concerning its effect on phytopathogenic fungi. Thus, the extent of the inhibitory effects exhibited by the combination of the two was quite surprising. Although 2-DG appears to adversely affect the growth of filamentous fungi including postharvest pathogens and some yeasts, it does not affect the growth of *C. saitoana* isolate 240 (FIG. 2), thereby allowing the exploitation of the inhibitory activity of the sugar analog and the antagonistic activity of the microorganism.

It is understood that the foregoing detailed description is given merely by way of illustration and that modifications and variations may be made therein without departing from the spirit and scope of the invention.

We claim:

1. A biologically pure culture of *Candida saitoana* having all of the identifying characteristics of deposited microorganism NRRL Y-21022, wherein the microorganism is antagonistic to fungal postharvest diseases of fruits and resistant to the fungicidal activity of 2-deoxy-D-glucose.

2. The biologically pure culture of claim 1, wherein said isolate is NRRL Y-21022.

3. A biocontrol composition comprising *Candida saitoana* having all of the identifying characteristics of deposited microorganism NRRL Y-21022 and 2-deox-D-glucose.

4. The biocontrol composition of claim 3, wherein said isolate is NRRLY-21022.

5. A method for the control of fungal postharvest diseases of fruits, said method comprising applying an effective amount of the biocontrol composition of claim 3.

6. The method of claim 5, wherein the effective amount of the microorganism is at a concentration of from about $10^7$ CFU/ml to about $10^9$ CFU/ml.

7. The method of claim 6, wherein said concentration of the microorganism is at about $10^8$ CFU/ml.

8. The method of claim 5, wherein the effective amount of 2-deoxy-D-glucose is a concentration of from about 0.01% (w/v) to about 1.0% (w/v).

9. The method of claim 8, where said concentration of 2-deoxy-D-glucose is about 0.05% (w/v) to about 0.1% (w/v).

* * * * *